United States Patent [19]

Stanbro

[11] Patent Number: 5,082,627

[45] Date of Patent: Jan. 21, 1992

[54] THREE DIMENSIONAL BINDING SITE ARRAY FOR INTERFERING WITH AN ELECTRICAL FIELD

[75] Inventor: William D. Stanbro, Columbia, Md.

[73] Assignee: Biotronic Systems Corporation, Rockville, Md.

[21] Appl. No.: 44,761

[22] Filed: May 1, 1987

[51] Int. Cl.$^5$ .......................................... G01N 27/00
[52] U.S. Cl. ................... 422/82.01; 204/403; 324/658; 324/663; 324/686; 422/68.1; 422/69; 422/70; 422/90; 422/98; 427/2; 427/79; 427/80; 427/81; 435/288; 435/291; 435/819; 436/525; 436/528
[58] Field of Search ............ 204/403; 324/60 R, 61 R, 324/61 C; 422/68, 70, 69, 90, 98, 82.01; 427/2, 79, 80, 81; 435/288, 291, 817; 436/525, 528, DIG. 80

[56] References Cited

U.S. PATENT DOCUMENTS

| | | |
|---|---|---|
| 4,072,576 | 2/1978 | Arwin et al. . |
| 4,233,402 | 11/1980 | Maggio et al. . |
| 4,453,126 | 6/1984 | Volgyesi . |
| 4,490,216 | 12/1984 | McConnell ........................ 435/817 |
| 4,571,543 | 2/1986 | Raymond et al. . |
| 4,637,861 | 1/1987 | Krull et al. ........................ 435/817 |
| 4,740,468 | 4/1988 | Deng et al. ........................ 435/805 |

FOREIGN PATENT DOCUMENTS 55-33449 3/1980 Japan .

OTHER PUBLICATIONS

Molecular Design for Electroanalysis, by Murray et al., Analytical Chemistry, vol. 59, No. 5, Mar. 1, 1987.
Kinetics of Electron-Transfer Cross-Reactions Within Redox Polymers . . . , by Anson et al., Journal of the American Chemical Society, vol. 105, No. 15, 1983, p. 4884.
New Model for the Interior of Polyelectrolyte Coatings on Electrode Surfaces . . . , by Anson et al., Journal of the American Chemical Society, vol. 105, No. 5, 1983, p. 1096.
"Affinity Chromotography", by I. Parikh et al., Aug. 26, 1985, Chemical and Engineering News, pp. 17–32.
"Affinity Chromotography", by R. Walters, Sep. 1985, Analytical Chemistry, vol. 57, No. 11, pp. 1099A–11-14A.
"Adsorption of Blood Proteins On Metals Using Capacitance Techniques", by Stoner et al., The Journal of Physical Chemistry, vol. 74, No. 5, Mar. 5, 1970.

Primary Examiner—Robert J. Warden
Assistant Examiner—Timothy M. McMahon
Attorney, Agent, or Firm—Leonard W. Pojunas, Jr.

[57] ABSTRACT

A dielectric material of a capacitive affinity sensor has a three-dimensional molecular binding site array. A glass base is layered with a binding agent like silane from which a polymeric backbone like polylysine extends. The polymeric backbone is prepared to accept receptor molecules like cortisol hemisuccinate to bind a specific antibody. Such an array changes dielectric properties between the two electrodes of the capacitive affinity sensor to greatly enhance sensitivity of the sensor.

2 Claims, 2 Drawing Sheets

THREE DIMENSIONAL BINDING SITE ARRAY FOR INTERFERING WITH AN ELECTRICAL FIELD

BACKGROUND OF THE INVENTION

Cross-reference is made to two U.S. Pat. Applications: Ser. No. 044,767, for Added Array Of Molecular Chains For Interfering With Electric Fields, by W.D. Stanbro et al.; and Ser. No. 044,769, now U.S. Pat. No. 4,769,121, for Sintered Pellet With Biochemically Active Layer, by A.L. Newman, which were filed the same date and were assigned to the same entity as this application.

The invention relates to a means for interfering with an electrical field. More specifically, the invention relates to electrodes of a capacitive affinity sensor that are insulated with a three-dimensional molecular binding site array.

In composition analysis, capacitive sensors have been used to determine the concentration of a specific gas in a mixture, or an analyte in a fluid, for example. Such sensors measure a capacitance that changes with the concentration.

Newman U.S. Pat. Application Ser. No. 799,761, filed Nov. 19, 1985, ("the Newman Patent Application") involves a capacitor for determining the concentration of an analyte in a fluid, for instance. Biospecific binding reactions occur in a space between electrodes of a capacitive sensor. These reactions occur among molecules of a binding agent immobilized on a surface and an analyte in a fluid. These reactions result in the displacement of small fluid molecules having high dielectric constants by large biochemical molecules having low dielectric constants. This displacement of molecules changes the dielectric constant of the capacitor.

Raymond et al. U.S. Pat. No. 4,571,543 discusses a capacitor for detecting and measuring the concentration of specific non aqueous materials or constituents in fluids. The capacitor is layered with a coating of silane and then a coating of certain polymers. These polymers form membranes that are permeable to constituents of the fluids. The constituents penetrate through the membrane to change the dielectric constant of a solution under the membrane.

Volgyesi U.S. Pat. No. 4,453,126 concerns a capacitor for monitoring the concentration of anaesthetic gas in a breathing mixture. The capacitor has a dielectric of lipids or elastomers which permit the absorption of the anaesthetic gas to vary electrical characteristics of the sensor.

"Adsorption Of Blood Proteins On Metals Using Capacitance Techniques", by Stoner et al., The Journal of Physical Chemistry, Vol. 74, No. 5, Mar. 5, 1970, describes a differential capacity method for measuring adsorption of proteins on solid metal electrodes.

Arwin et al. U.S. Pat. No. 4,072,576 relates to a capacitive method for studying enzymatic activity and for studying an immunological reaction. An adsorbed polypeptide substrate is used to study enzymatic activity and an antigen is adsorbed onto an electrode surface to study the reaction of the antigen with an antibody.

Molecular Design for Electroanalysis, by Murray et al., Analytical Chemistry, Vol. 59, No. 5, March 1, 1987, discusses chemically modified electrodes for use in sample analysis, and the use of electroactive polymer films, like poly-L-lysine, on such electrodes. These films facilitate oxidation-reduction reactions at the electrodes.

Kinetics of Electron-Transfer Cross-Reactions within Redox Polymers; Coatings of a Protonated Polylysine Copolymer with Incorporated Electroactive Anions, by Anson et al., Journal of the American Chemical Society, Vol. 105, No. 15, 1983, p. 4884, describes electrodes coated with polymer layers that form a three dimensional arrangement of catalytic sites. These layers comprise a random orientation of polymer coils to facilitate oxidation reduction reactions at the electrode. New Model for the Interior of Polyelectrolyte Coatings on Electrode Surfaces; Mechanisms of Charge Transport through Protonated Poly(L-lysine) Films Containing $Fe^{III}(edta)-$ and $Fe^{III}(edta)^{2-}$ as Counterions, by Anson et al., Journal of the American Chemical Society, Vol. 105, No. 5, 1983, p. 1096, also describes such electrodes.

In composition analysis, affinity chromotography has been used to determine the presence or concentration of an analyte in a fluid. The analyte is chemically separated or isolated from the fluid, as described in two articles entitled "Affinity Chromotography", one by I. Parikh et al., Aug. 26, 1985, Chemical and Engineering News, pp. 17-32 and the other by R. Walters, Sept., 1985, Analytical Chemistry, Volume 57, No. 11, pp. 1099A-1114A.

Maggio et al. U.S. Pat. No. 4,233,402 deals with the chemical analysis of an analyte on a substrate using hub nuclei that spread along the substrate and to which ligands are covalently bound.

SUMMARY OF THE INVENTION

The invention concerns an apparatus, and a method for making the apparatus, comprising a base layer, an electrical field generating means on the base layer, and an electrical field interfering means. The electrical field interfering means has a polymer backbone having a means for accepting a receptor molecule. A means is provided to bind the polymer backbone to and extend the polymer backbone from the base layer. In one embodiment, the electrical field generating means is an electrode of a capacitive affinity sensor, for instance.

In that embodiment, a biochemical layer is provided between electrodes of the sensor. The biochemical layer has greatly decreased dielectric properties and a greatly increased thickness. Thus, the capacitance of the biochemical layer is greatly decreased. Such a biochemical layer is used to provide a very sensitive capacitive affinity sensor, for instance.

DETAILED DESCRIPTION

Figure 1:
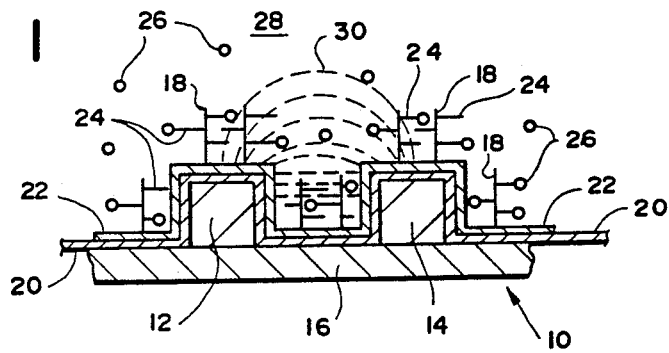
FIG. 1 shows electrodes of a capacitive affinity sensor with a dielectric material according to this invention.

Capacitive affinity sensors measure the concentration of an analyte by detecting a change in capacitance as an analyte molecule moves in or out of an electric field between two electrodes of the sensor, for instance. The moving analyte molecule has a low dielectric constant and displaces solvent molecules having higher dielectric constants from a biochemically active layer between the two electrodes. The displacement of the solvent molecules by the analyte molecules reduces capacitance between the two electrodes. The capacitance between the two electrodes is inversely proportional to the concentration of the analyte being measured by such a sensor.

Other capacitances are present in a capacitive affinity sensor and include the capacitance of any passivating layers over the electrodes and the capacitance of the solvent about the electrodes. The capacitances of the sensor add as follows:

$$C_T = \frac{1}{\sum_{i=1}^{n} \frac{1}{C_i}} \quad (1)$$

where $C_T$ is the total capacitance of the sensor and $C_i$ is the capacitance of each of the biochemically active layer, the passivating layer and of the solvent. For an idealized parallel plate capacitor, the individual capacitances are proportional to the ratio of the dielectric constant and the distance between the parallel plates. That is $$C_i \alpha \frac{\epsilon_i}{d_i} \quad (2)$$

where $\epsilon_i$ is the dielectric constant and $d_i$ is the distance between the parallel plates. This type of situation applies regardless of the actual geometry of the plates.

A typical passivating layer of a capacitive affinity sensor is about 2000 Angstroms thick and provides an impervious pin-hole free barrier to water and ions. A solvent layer can be several microns thick. However, in a sensor as discussed in the Newman Patent Application, antibodies extend about 100 Angstroms above an insulator surface in the biochemically active layer. Thus, such a biochemically active layer is thin compared to the passivating layer and the solvent layer. According to equation (2) the capacitance of such a biochemically active layer is large compared to that of any passivating layers and solvent. According to equation (1) the dominant capacitance in the total capacitance $C_T$ is that of the layer having the lowest capacitances. Thus, it is desirable to minimize the capacitance of the layer of an affinity sensor that is modulated, such as the biochemically active layer, to maximize the sensitivity of such a sensor. Minimizing the capacitance of the biochemically active layer brings the capacitance of this layer into the ranges of the other capacitances in the sensor.

The capacitance of the biochemically active layer is affected by the presence or absence of the large analyte molecules in the solvent, for instance. According to equation (2) capacitance decreases with decreasing $\epsilon_i$ or increasing $d_i$. This invention concerns a means for increasing $d_i$. This invention also concerns a means for increasing the difference between capacitances that are measured when all the large molecules enter the electric field and when all leave the electric field.

FIG. 1 shows schematically a capacitive affinity sensor 10 with electrodes 12 and 14 insulated according to this invention. The sensor 10 has a base layer 16 that supports the two electrodes 12 and 14, which have opposite polarities. The base layer 16 comprises a substrate of insulating material like alumina.

A passivating layer 20 covers the base layer 16 and electrodes 12 and 14 in the preferred embodiment of this invention. A binding agent 22 covers the passivating layer 20. This binding agent 22 binds polymeric backbones 18 to the base layer 16. These polymeric backbones 18 extend roughly at right angles to any surface covered by the binding agent 22. There are a number of potential materials for the backbone including polynucleotides, polysaccharides, polystyrenes and polypeptides. Though not shown, horizontal polymeric backbones extend from any vertical surfaces covered by the binding agent 22.

Molecules form receptors 24 that branch from the polymeric backbone 18. Each receptor 24 is a potential binding site for a molecule of a specific analyte 26. The receptors 24 are located, not only in a plane parallel to the surface of the binding agent 22, but at different distances above the binding agent 22. The receptors 24 are located at different heights of the polymeric backbone 18. Thus, a three dimensional array of receptors 24 is provided for molecules of the analyte 26.

This array of receptors 24 allows a greater number of analyte molecules 26 to bind in the electric field 30 between the electrodes 12 and 14, compared to the number of analyte molecules 26 that could bind to receptors located only along the surface of the binding agent 22. Also, this greater number of analyte molecules 26 bind and then displace a greater amount of high-dielectric constant solvent 28 from the electric field 30.

The use of a three dimensional array of receptors 24 greatly increases the thickness $d_i$ and greatly changes the dielectric properties of a biochemical layer in a capacitive affinity sensor. According to equation (1), the capacitance between electrodes 12 and 14 will greatly decrease.

Figure 2:
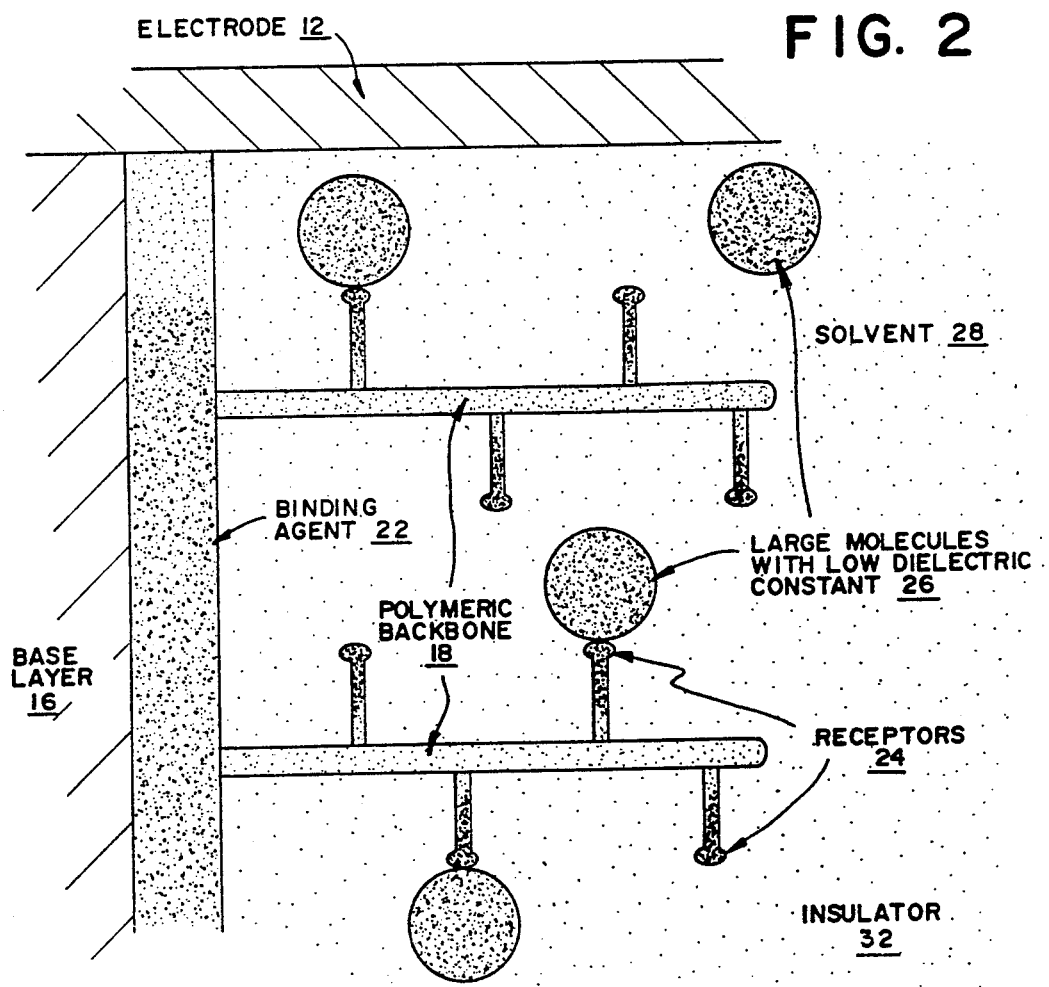
FIG. 2 shows schematically an electrode insulated with a structure having a three dimensional array of molecular binding sites.

FIG. 2 shows schematically a detail of the three dimensional array of receptors 24. The binding agent 22 covers the base layer 16 and binds the polymeric backbones 18 to the base layer 16. Receptors 24 are located along the polymeric backbones 18 at different distances from the binding agent 22 and the base layer 16. Large molecules 26 of an analyte travel through the solvent 28 and bind to the receptors 24. The receptors 24 are biospecific to the large molecules 26 of the analyte, for instance.

The base layer 16, polymeric backbones 18, binding agent 22, receptors 24 are adjacent to, and in the electrical field of, an electrode 12 of a capacitive affinity sensor as shown in FIG. 1, for instance. These elements 16, 18, 22, 24 and 28 in this electric field form an electrical insulator 32 for a single electrode 12 as shown in FIG. 2. However, in the preferred version, the base layer 16, polymeric backbones 18, binding agent 22, receptors 24, and solvent 28 form a dielectric material between two electrodes of a capacitive affinity sensor.

As discussed above concerning the affinity sensor 10 of FIG. 1, the large analyte molecules 26 have low dielectric constants and displace the solvent molecules 28 having a high dielectric constant as the analyte molecules 26 bind to the receptors 24. Thus, the insulating qualities of the insulator 32 vary proportionally with the concentration of analyte molecules 26 in the solvent 28.

FIG. 2 shows the insulator 32 adjacent one electrode 12. The relative arrangement of the insulator 32 and electrode 12 is easily varied. For instance, a passivating layer 20 and the binding agent 22 may cover both the electrode 12 and the base layer 16 as shown in FIG. 1. The passivating layer 20 and binding agent 22 may cover only the base layer 16, in which case the binding agent 22 may contact the electrode 12 as shown in FIG. 2 or may be spaced from the electrode 12. The insulator 32 is adjacent the electrode 12 when both are arranged so the insulator 32 substantially interfers with the electric field of the electrode 12.

Figure 3:
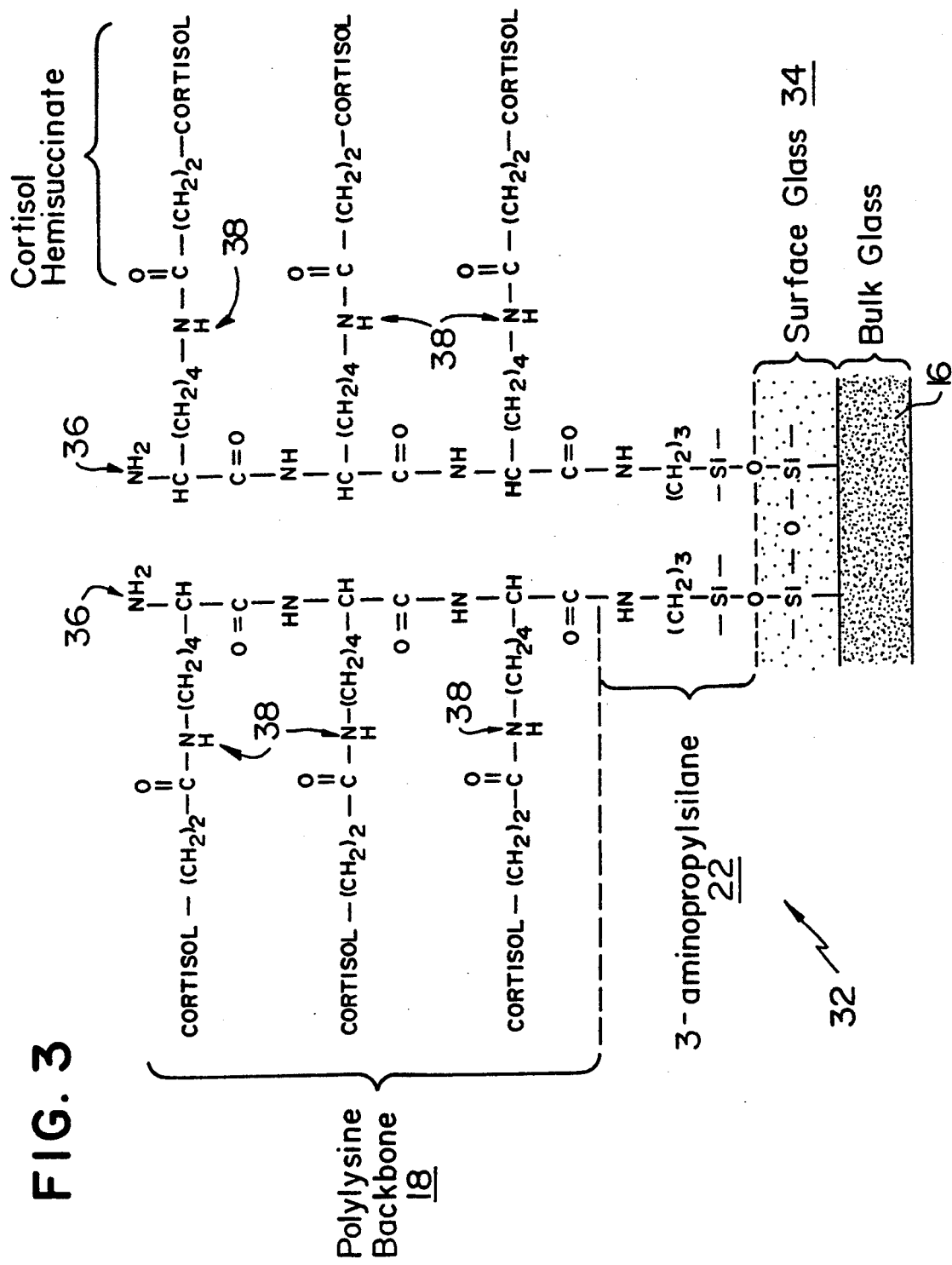
FIG. 3 shows one composition of the three dimensional array of FIG. 2.

FIG. 3 shows one composition for the insulator 32 of Figure 2. The first step in forming this composition is the preparation of a silanized surface. The base layer 16 is glass-like such as silica with an SiOH layer. The base layer 16 is dipped in a 2% solution of 3-aminopropyltriethoxy silane in 95% ethanol for 1 to 2 minutes. This forms the silanized surface which is set aside for a number of hours to cure. Other silanes may be used such as:
phenyltriethoxysilane,
chloropropyltriethoxysilane,
vinyltriethoxysilane,
allyltriethoxysilane, and
ethoxysilane.

The next step is the preparation of polylysine backbone protected amino groups. Amino groups of the polylysine backbone are to be protected with N-carbobenzoxy ("CBZ") on the $\alpha$ nitrogen 36 and the $\epsilon$ nitrogen 38 to prevent cross binding of the polylysine to itself, instead of only to the silane binding agent 22. The $\alpha$ nitrogen 36 can be protected by treating the polylysine with CBZ chloride. Polylysine with CBZ protected $\epsilon$ nitrogens 38 is commercially available from Sigma Chemical Company. Some examples are:
poly-$\epsilon$-CBZ-D-lysine, No. P6256
poly-$\epsilon$-CBZ-DL-lysine, No. P2883
poly-$\epsilon$-CBZ-L-lysine, No. P4510 (1000–4000 molecular weight) and
poly-$\epsilon$-CBZ-L-lysine, and P9503 (200000–500000 molecular weight).

Next, the polylysine with protected nitrogens 36 and 38 is connected to the silane covered base layer of the sensor. The sensor is immersed in phosphate buffered saline having a pH of 6.4, with 1-ethyl-3-(3)-dimethylaminipropyl (carbodiimide), known as EDC, and the polylysine is then added. The polylysine binds to the silane binding agent and forms a backbone 18 substantially perpendicular to the base layer 16. The CBZ is then removed by catalytic hydrogenation.

The final step is the addition of a linking molecule with a biospecific receptor 24, to the $\epsilon$ nitrogens 38 of the polylysine backbone 18. In this final step, the sensor is immersed again in phosphate buffered saline with EDC to which cortisol hemisuccinate is added, for instance. The hemisuccinate attaches as one example of the linking molecule and the cortisol as one example of the biospecific receptor 24. Alternately, the cortisol could be attached directly to the polypeptide without a linking molecule. With or without a linking molecule, the biospecific receptor 24 is chosen to bind with a specific analyte.

Examples of biospecific receptors are discussed in the Newman Patent Application. The following chart lists other examples of receptors and analytes that are biospecific to and, therefore, bind to one another.

| Receptors | Analytes |
|---|---|
| Antigen | Antibody |
| Hapten | Antibody |
| Enzyme | Substrate Chemical |
| Lectin | Carbohydrate |
| Hormone | Hormone Receptor |
| Hormone | Binding Globulin |
| Neuroreceptor | Neurotransmitter |
| DNA | RNA |
| DNA | DNA |
| RNA | RNA |

These receptors and analytes are reversible. For instance, when an antibody is bound as a biochemically active layer, a biospecific antigen diffuses through a solvent to bind onto that antibody.

A polypeptide backbone with a cortisol receptor is ideal for a capacitive affinity sensor using competitive binding. A capacitive affinity sensor using competitive binding is described in the Newman Patent Application. This patent also describes a sensor using direct binding.

According to the present invention, a capacitive affinity sensor using direct binding has a cortisol receptor 24 that attaches to the polypeptide backbone. The cortisol receptor will bind with an analyte of cortisol binding globulin.

A polysaccharide may also be used as the polymeric backbone. An example of such a polysaccharide is cyanogen bromide activated agarose. This agarose would bind with a 3-aminopropylsilane group on the surface of a base layer, using EDC as a catalyst in a solvent like water or alcohol. The agarose is then reacted with a linking molecule such as 1, 4-diaminobutane, again using cyanogen bromide to activate the agarose and using EDC as the catalyst.

A polynulceotide may be used as the polymeric backbone. An example of such a polynucleotide is polyadenylic acid, which is commercially available from Sigma Chemical Company, No. P9403. Amino groups of the andenylic acid units are protected by attaching acetyl groups to them. Then the terminal phosphoryl groups of the andenylic acid units are attached to an amino silane on the base layer of a sensor using EDC as a catalyst. The protecting acetyl groups are then removed from the amino groups by treating the sensor with ammonium hydroxide. Finally, the cortisol hemisuccinate would be attached to the adenylic acid amino groups using EDC as a catalyst.

According to a preferred version of this invention, polymeric backbones form a biochemically active layer comprising a three dimensional binding site array for analyte molecules. This array thickens a dielectric material of a capacitive affinity sensor and drastically affects the dielectric properties of the sensor. The array enhances the sensitivity of the sensor to an analyte in a solution, for example.

What is claimed is:

1. An apparatus for detecting an analyte comprising:
an electrode for generating an electrical field;
a means for interfering with the electrical field comprising a biochemically active layer that comprises a plurality of polylysine backbones, and a silane for binding each polylysine backbone and extending each polylysine backbone into the electrical field; and
a means for enhancing interference with the electrical field according to a concentration of an analyte, comprising a plurality of receptor molecules biospecific to the analyte and bound to and extending from each polylysine backbone, each receptor molecule being biospecific to the analyte.

2. A capacitive affinity sensor for detecting an analyte comprising:
   a means for generating an electrical field comprising two electrodes having opposite polarities;
   a means for interfering with the electrical field comprising a dielectric material between the two electrodes, the dielectric material comprising a biochemically active layer of a plurality of polylysine backbones and a means for binding each polylysine backbone and extending each polylysine backbone into the electric field and
   a means for enhancing interference with the electrical field according to a concentration of an analyte, comprising a plurality of binding sites on each polylysine backbone, each binding site comprising a receptor molecule biospecific to the analyte and bound to and extending from a polylysine backbone.

* * * * *